United States Patent [19]

Succi et al.

[11] Patent Number: 5,343,735

[45] Date of Patent: Sep. 6, 1994

[54] APPARATUS FOR ACCURATELY MEASURING THE WATER CONTENT OF GASES

[75] Inventors: Marco Succi, Milan; Carolina Solcia, Grezzago; Fabrizio Doni, Milan; Antonio Coppola, Turate, all of Italy

[73] Assignee: SAES Getter S.p.A., Milan, Italy

[21] Appl. No.: 967,030

[22] Filed: Oct. 27, 1992

[30] Foreign Application Priority Data

Nov. 6, 1991 [IT] Italy ................ MI-A002941

[51] Int. Cl.⁵ ............................... G01W 1/11
[52] U.S. Cl. ................. 73/29.01; 73/335.02; 73/335.03; 73/335.04; 73/29.02; 204/153.22; 204/430
[58] Field of Search ........... 73/29.01, 29.02, 335.03, 73/335.04, 335.02; 204/153.22, 430

[56] References Cited

U.S. PATENT DOCUMENTS

| | | |
|---|---|---|
| 2,830,945 | 4/1958 | Keidel . |
| 2,900,317 | 5/1959 | Keidel . |
| 2,993,853 | 7/1961 | Berry . |
| 3,146,181 | 8/1964 | Bell . |
| 3,147,202 | 9/1964 | Johnson . |
| 3,166,928 | 1/1965 | Jackson et al. ............ 73/335.01 |
| 3,244,602 | 4/1966 | Glass . |
| 3,630,875 | 12/1971 | Kuffer . |
| 3,799,846 | 3/1974 | Capuano . |
| 3,926,052 | 12/1975 | Bechtel ....................... 374/20 |
| 3,926,745 | 12/1975 | Czuha . |
| 4,280,885 | 7/1981 | Savery . |
| 4,800,000 | 1/1989 | Zatko . |
| 4,946,288 | 8/1990 | Siska et al. ................ 374/20 |
| 5,139,344 | 8/1992 | Mutter ....................... 374/28 |

OTHER PUBLICATIONS

Melcor–Frigichip ® Minature Ceramic Modules, Series FC 47 pages.

Primary Examiner—Timothy M. McMahon
Attorney, Agent, or Firm—David R. Murphy

[57] ABSTRACT

An apparatus for accurately measuring the water content of a moist gas containing less than 50 parts per million (ppm) of water comprises an isothermal heat-sink (14), a radiator (20), a Peltier heater-cooler (24) thermally arranged between the isothermal heat-sink (14) and the radiator (20). The heater-cooler (24) is transferring heat from the isothermal heat-sink (14) to the radiator (20) and vice versa. A phosphoric acid moisture cell (32) is in thermal contact with the isothermal heat-sink (14). Upon passing the moist gas through the cell (32) the amount of moisture in the moist gas is measured as variation of electrical current throughout the cell.

5 Claims, 4 Drawing Sheets

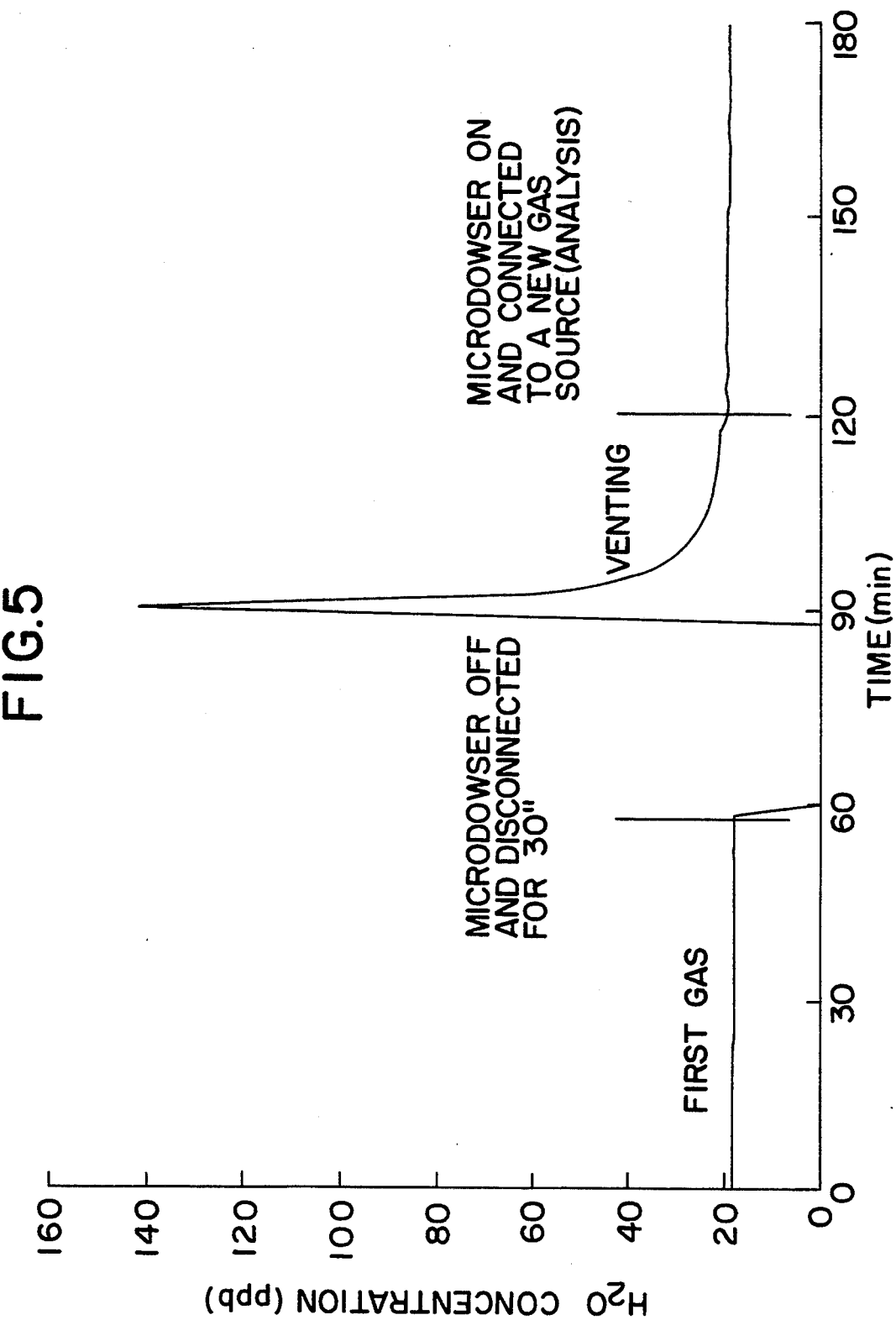

APPARATUS FOR ACCURATELY MEASURING THE WATER CONTENT OF GASES

BACKGROUND OF THE INVENTION

1. Field of the Invention

The invention relates to an apparatus for accurately measuring the water content of a moist gas containing less than 50 ppm or even less than 10 ppb of water.

2. The Prior Art

Apparatuses for accurately measuring the water content of gases are well known and are frequently referred to as moisture analyzers. One important class of moisture analyzers are those which rely on moisture-induced changes in the electrical resistance of phosphoric acid ($P_2O_5$) which is contained within a cell of the analyzer. Such moisture analyzers are described for example in the following U.S.A.

| U.S. Pat. No. | Hereinafter occasionally referred to as: |
|---|---|
| 2,830,945 | "Keidel '945" |
| 2,900,317 | "Keidel '317" |
| 2,993,853 | "Berry" |
| 3,146,181 | "Bell" |
| 3,147,202 | "Johnson" |
| 3,244,602 | "Glass" |
| 3,630,875 | "Kuffer" |
| 3,799,846 | "Capuano" |
| 3,926,745 | "Czuha" |
| 4,280,885 | "Savery" |
| 4,800,000 | "Zatko" |

There is no agreement, in the prior art, as to the operating temperature of the cell. Johnson discloses the use of a cooling coil and states that the "... temperature ... preferably is in the range from about 0° to about 50° F. ($-18°$ to $10°$ C.)". Czuha disagrees and claims a method wherein his "phosphoric acid solution is maintained at a temperature of at least about 50° C.".

In order to maintain the cell, according to Johnson, below room temperature, let us say 20° C., it is necessary to remove heat from the cell. Most of the readily available cooling means however suffer from a lot of drawbacks; in particular the use of tap water requires a source and excludes the use of the analyzer in the field. The use of phase changing refrigerants, like the CFC, suffer from a multitude of drawbacks. All the phase changing products are requiring a compressor in order to change their phase back to liquid for continued use, and the chloro-fluorinated hydrocarbons (CFC) damage the ozone layer of the atmosphere if they escape. Many jurisdictions are considering passing laws restricting their use for cooling purposes.

As is well known in the art the phosphoric acid must be completely dry when first contacted with the moist gas to be measured. It is therefore common practice to cycle the cell by periodically increasing the current through the cell. Examples of this cycling are shown in Bell (FIG. 2), Glass (FIG. 4), Kuffer (FIGS. 1 and 2) and Capuano (FIG. 3). However what the prior art in general and these references in particular have not identified are the problems which occur when a large amount of moist gas is in the system upstream of the cell. These problems include slow cell response times, possible inaccuracies and an inability to measure small moisture concentrations equal to or lower than one part per million.

Accordingly it is an object of the present invention to provide an apparatus for accurately measuring the water content of a moist gas, which apparatus is substantially free from one or more of the problems of the prior apparatuses.

Another object is to provide an improved apparatus which does not employ tap water, nor a phase changing refrigerant, nor a chlorinated hydrocarbon, nor a fluorinated hydrocarbon.

Yet another object is to provide an improved analyzer which has a fast cell response time.

Still another object is to provide an improved analyzer which can measure the moisture content of a gas even down to less than one part per million.

DISCLOSURE

The above and other objects are accomplished, according to the present invention, by providing an improved apparatus designed by the Applicant. More precisely, the invention relates to an apparatus for accurately measuring the water content of a moist gas containing less than 50 parts per million of water. The apparatus comprises: an isothermal heat-sink; a radiator; a Peltier heater-cooler, thermally arranged between the isothermal heat-sink and the radiator (the heater-cooler is transferring heat from the isothermal heat sink to the radiator and vice versa). The apparatus further comprises: a phosphoric acid moisture cell in thermal contact with the isothermal heat-sink; means for passing the moist gas through the cell; and means for measuring an electrical current in the cell and thereby determining the amount of moisture in the moist gas.

The apparatus of the present invention can be used to analyze the water content of any gas which does not react with phosphoric acid. Examples of suitable gasses include: air, nitrogen, oxygen, carbon dioxide, carbon monoxide, hydrocarbons, such as methane, ethane and benzene, and noble gases such as argon, helium and neon.

The invention may be better understood by reference to the following drawings which are supplied for illustrating purposes but do not limit in any way the scope of the invention.

BRIEF DESCRIPTION OF THE DRAWINGS

FIG. 5 is a graph showing the relationship of current over time, when measuring the moisture content of a typical gas.

Figure 1:
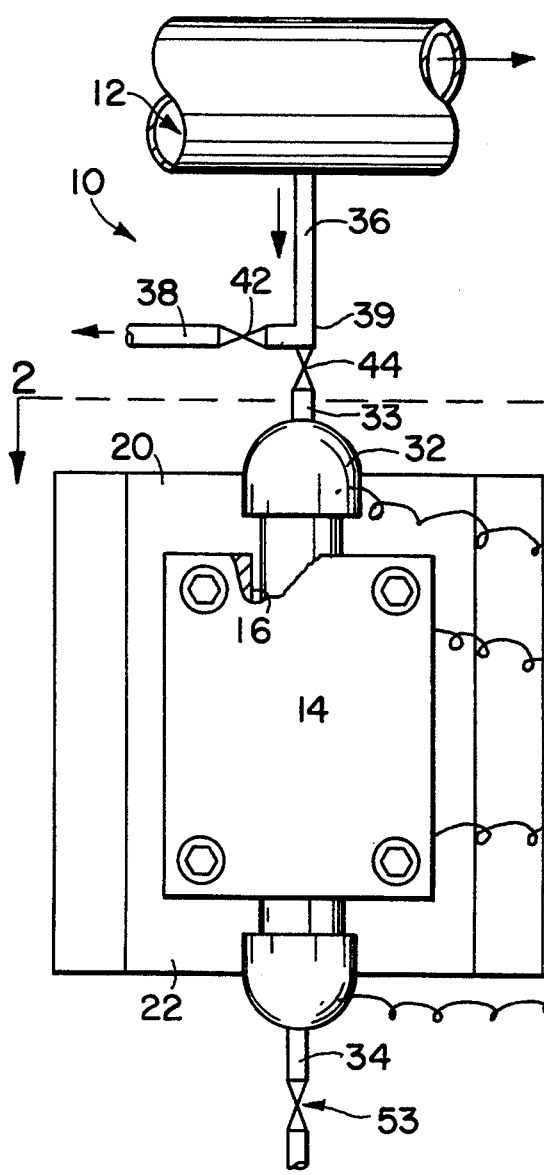
FIG. 1 is an elevation view of an apparatus of the present invention.
Figure 2:
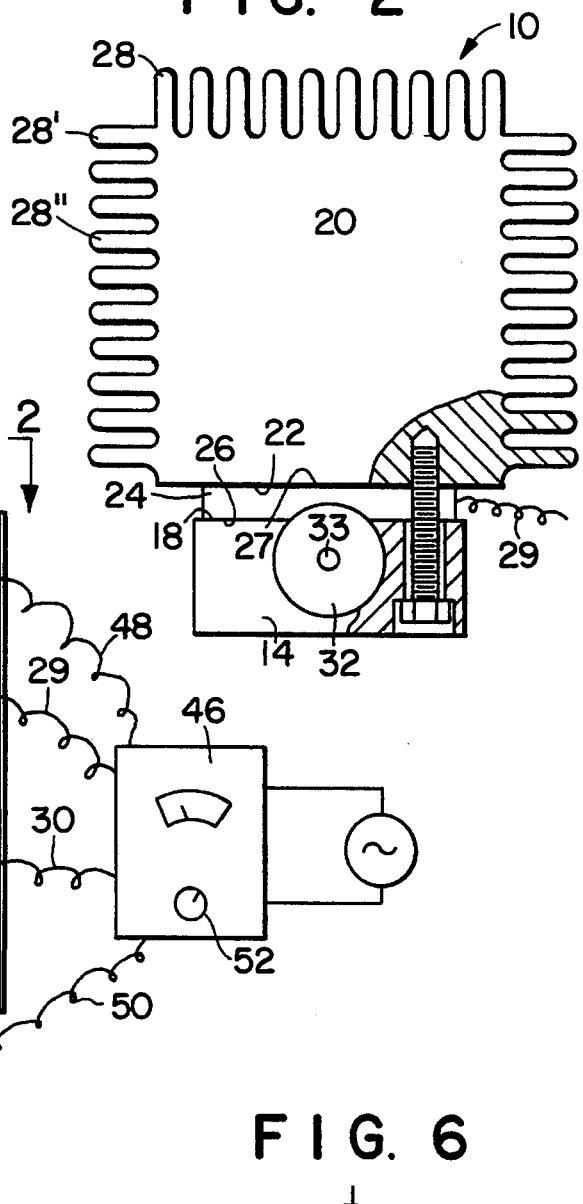
FIG. 2 is a plan view taken along line 2—2 of FIG. 1.
Figure 6:
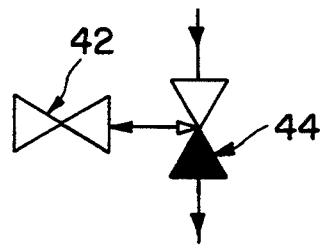
FIG. 6 shows alternative self explanatory details for the valving system.

Referring now to the drawings in general and in particular to FIGS. 1 and 2 there is shown an apparatus 10 for accurately measuring the water content of a moist gas source 12. The moist gas source 12 is preferably maintained at superatmospheric pressure. However, in the broadest aspects of the present invention, the pressure of the moist gas can be subatmospheric as long as there is a pressure difference sufficient for the moist gas to flow through the apparatus 10. The moist gas can contain widely varying amounts of water. However the apparatus is especially useful for measuring the water content of moist gases having less than one part per million of water. Because of the great improvement, represented by this invention, the new apparatus can analyze moisture contents of less than 50 and preferably 30 parts per billion (ppb) and even 10 parts per billion (ppb).

The apparatus 10 has a metal isothermal heat-sink 14. Within the isothermal heat sink 14 is a cylindrical recess 16. The heat sink 14 is also provided with a planar heat conducting surface 18.

The apparatus 10 has a metal radiator 20 which has a planar heat conducting surface 22, which is parallel to and juxtaposed a distance from the planar heat-conducting surface 18 of the isothermal heat sink 14.

The apparatus 10 is provided with a Peltier heater-cooler 24 which has a first heat transfer surface 26 parallel to the heat transfer surface 18 of the heat sink 14; and has a second heat transfer surface 27 parallel to the heat transfer surface 22 of the radiator 20. Thus the heat transfer surfaces 26, 27 of the heater-cooler 24 are thermally disposed between the heat transfer surface 18 of the isothermal heat-sink 14 and the heat transfer surface 22 of the radiator 20. The first heat transfer surface 26 is in contact with the isothermal heat sink 14. The second heat transfer surface 27 is in contact with the radiator 20.

Electrical direct current can be passed through the Peltier heater-cooler 24 in either of the two directions by means of the conductors 29, 30. In one direction heat is transferred from the surface 26 to the surface 27. In the other direction heat is transferred from the surface 27 to the surface 26. By the choice of current direction it is possible to heat one surface 26 or 27 and cool the other surface 27 or 26. Passing the current in either direction through the heater-cooler 24 serves to maintain the isothermal heat-sink 14 at its desired temperature, preferably at less than 20° C. and even better between 0° and 15° C. Heat is transferred to or from the ambient by conduction, convection and radiation, all of which is facilitated by fins on the radiator such as the fins 28, 28', 28''.

The apparatus 10 is also provided with a phosphoric acid moisture cell 32 within the cylindrical recess 16 of the isothermal heat-sink 14. The cell 32 is in thermal contact with the isothermal heat-sink 14, such that the cell 32 and the heat sink 14 always have the same temperature. The cell 32 has a moist gas inlet 33, and a gas outlet 34. Cells useful in the present invention are well known in the art and their description can be retrieved in Keidel '945, Keidel '317 and Zatko.

The apparatus 10 has a conduit 36 in fluid communication with the moist gas source 12 and the inlet 33 of the cell 32. A purge line 38 is in fluid communication with the conduit 36. The junction 39 of the purge line 38 with the conduit 36 is upstream of the cell 32. There is a valve 42 in the purge line 38 immediately adjacent to the junction 39. There is an isolation valve 44 in the conduit 36 downstream of junction 39 and immediately adjacent to the junction 39 and there is an outlet isolation valve 53 downstream of the cell 32.

The apparatus 10 is provided with an analyzer 46 for measuring the electrical current in the cell 32 and thereby determining the amount of moisture in the moist gas from the source 12. As is well known in the art, the analyzer 46 impresses a potential across the phosphoric acid cell 32 by means of conductors 48, 50.

The desired temperature of the cell 32 is set on the knob 52. The analyzer 46 compares this desired temperature with the actual temperature of the cell 32 and causes current to flow through the conductors 29, 30 to either heat or cool the cell 32 in order to maintain it at the desired temperature. The heater-coolers 24 are described for instance in the treatise "Solid State Cooling with Thermoelectrics" edited by MELCOR (Trenton J. J., USA), particularly in the chapter "Frigichip Miniature Ceramic Nodules—Series FC". A particularly useful heater-cooler is the one traded as Frigichip "CP 1.4-71-06L".

In operation, the temperature is set by Knob 52; moist gas flows from the source 12 through the conduit 36 and into the cell 32. The moisture in the moist gas changes the electrical resistance of the phosphoric acid in the cell, making the cell a variable resistor. The current flowing through this variable resistor is measured by the analyzer 46 as the percentage of moisture in the moist gas.

Cooling by Peltier effect in general, and by the particular structure described herein, avoids the use of tap water and of phase changing refrigerants. Furthermore the particular structure, including the valves 42, 44 and 53, grouped about junction 39 minimizes the amount of gas in the system from the last test and allows testing from different sampling lines to be carried out in a very short time.

Figure 3:
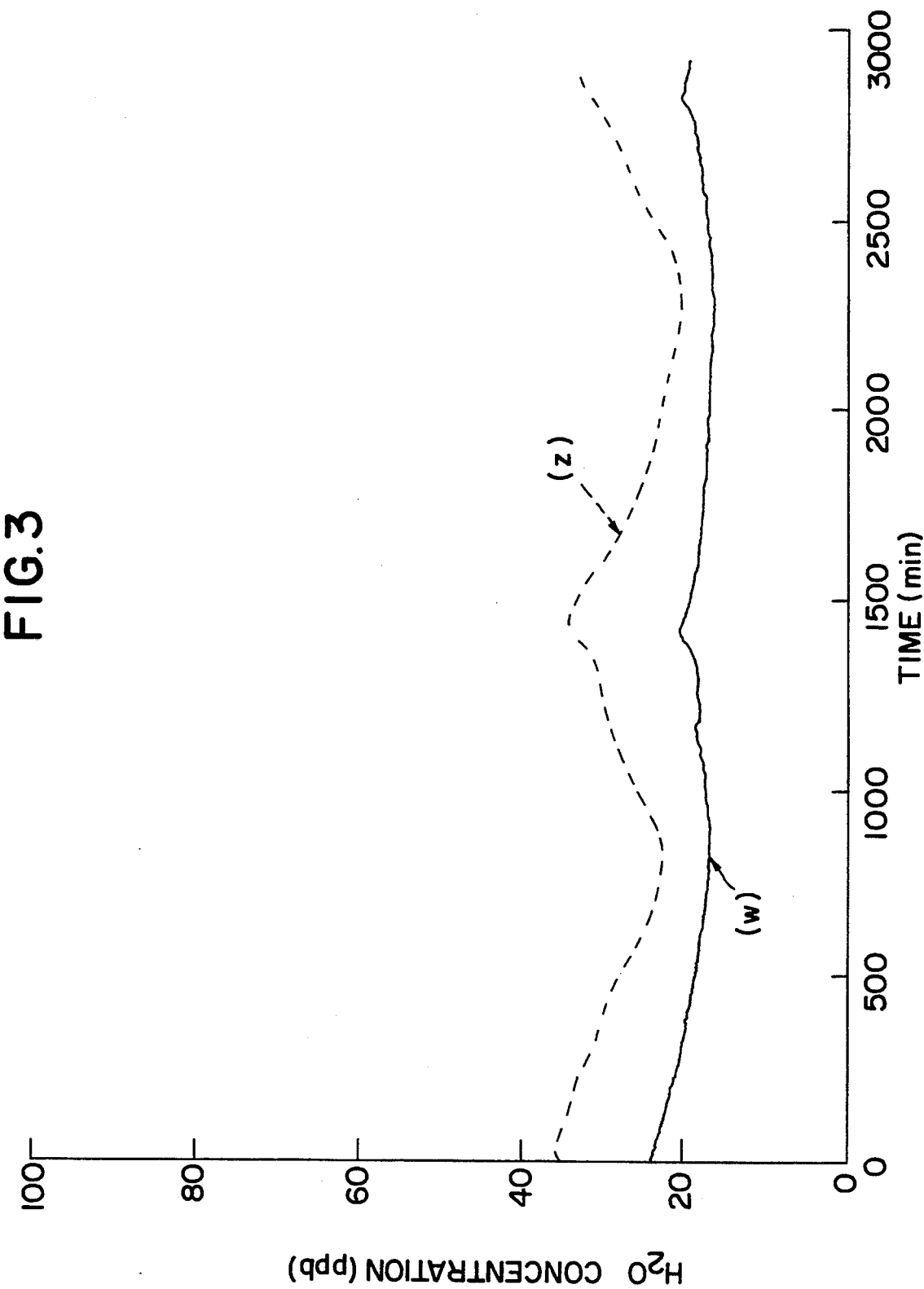
FIG. 3 is a graph showing the impact of thermoregulation, hence of the temperature changes, on the performance of the phosphoric acid moisture cell along the time.

Referring now to FIG. 3, there is reported the water content, along the time, of two streams of dry argon measured with a thermoregulated $H_3PO_4$ cell (line W: T=15° C.) and through a not thermoregulated cell (line Z). The wider excursion of line Z shows the impact of the temperature changes on the cell performance and clearly proves how it is necessary to thermoregulate the cell.

Figure 4:
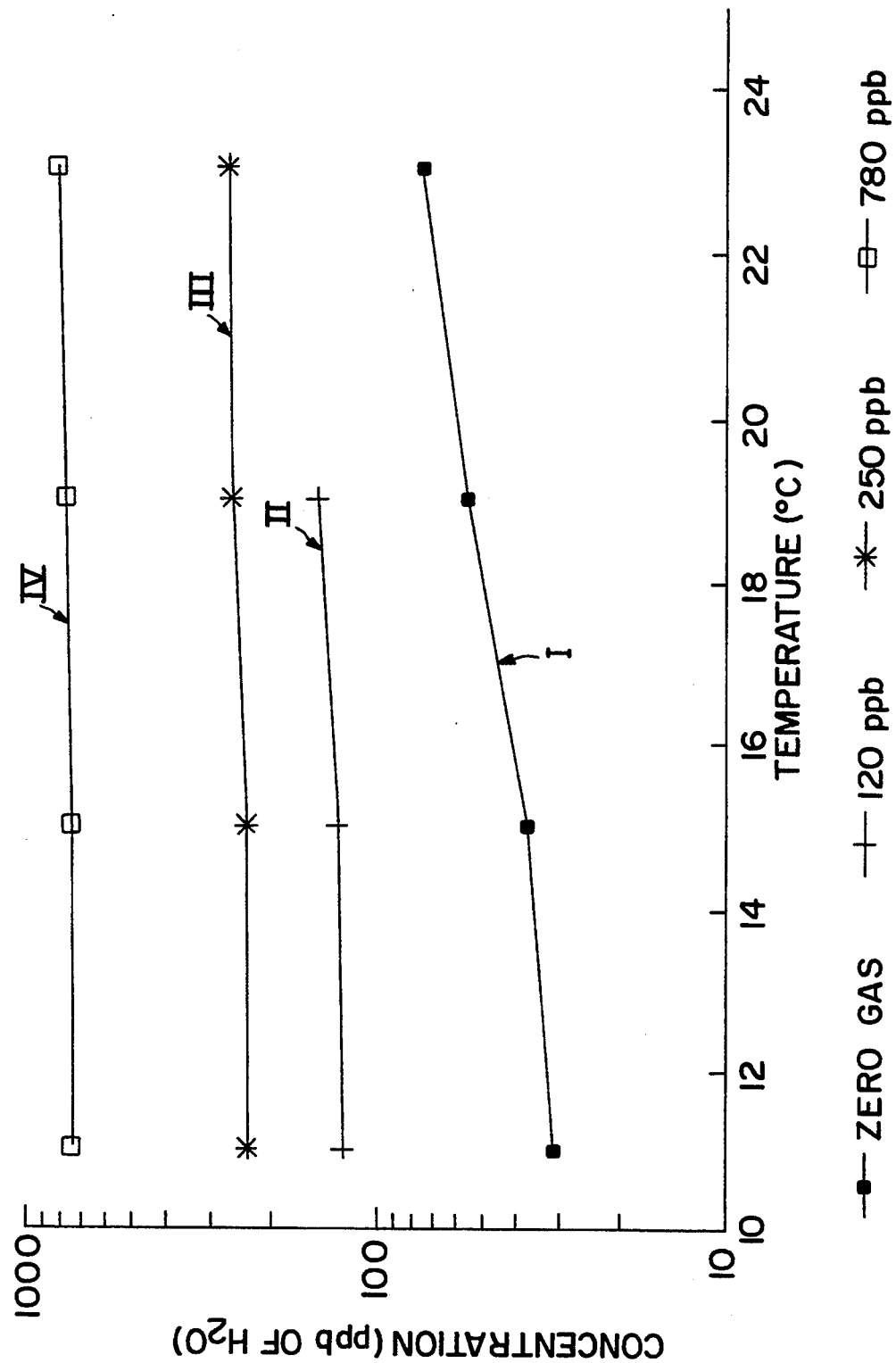
FIG. 4 is a graph showing how critical is the control of the temperature, in order to get satisfactory performance of the moisture cell.

Referring now to FIG. 4, there is reported the water content, along with the temperature, after the passage through a moisture analyzer, traded by the Applicant as MICRODOWSER and containing a thermoregulated cell (MICRODOWSER CELL 47A), of four different streams of argon, containing the following different amount of moisture

| stream | moisture (ppb) |
| --- | --- |
| I | practically absent |
| II | 120 ppb |
| III | 250 ppb |
| IV | 780 ppb |

From the lines II-IV on the figure, it is clear that in the case of a wet gas the final water content, in the range from 11° to 23° C., is indicatively constant. On the contrary, when the gas is dry (ZERO GAS; line I) temperature exerts a remarkable impact on the background noise; in fact, consequently to a temperature decrease from 23° C. to 15° C., the background noise is reduced to less than 50% of the original value.

This graph, in other words, is showing that the optimum temperature is lying between 10° and 15° C.; there is no need therefore for the expensive cryogenic devices required by the low temperatures of Johnson (down to −18° C.).

Referring now to FIG. 5, a first stream, consisting of dry argon, is passed through a moisture analyzer according to the invention (thermoregulated at 15° C. and supplied with MICRODOWSER CELL 47A); the water content, at the cell outlet, is 18 ppb, as recorded on the figure. Valves 42, 44 and 53 (see FIG. 1) are then closed and the isolated cell remains consequently separated from the air moisture. The analyzer is subsequently disconnected and connected to a new gas source, supplying a new gas. By always keeping the cell isolated (namely by keeping isolation valves 44 and 53 closed), valve 42 is opened and the inner pipes of the analyzer (outside the cell) are vented with a stream of purge gas, thus removing the air and the moisture penetrated during the transfer operation). Eventually, the isolation valves (44 and 53) are re-opened and a new (second) analysis can be carried out. By this method, the time required by each of several analysis tests is greatly reduced (from 2 to 3 hours, against the 24 hours required by the analyzers of the prior art).

Although the invention has been described in considerable detail with respect to preferred embodiments thereof, it will be understood that variations and modifications can be made without departing from the spirit and scope of the invention as described above and in the appended claims.

We claim:

1. An apparatus for accurately measuring, at a given measuring temperature within the range of about 0° to about 20° C., the water content of a moist gas containing less than 50 parts per million (ppm) of water comprising:
  A. an isothermal heat sink;
  B. a radiator;
  C. a Peltier heater-cooler thermally arranged between the isothermal heat sink and the radiator, wherein said heater-cooler transfers heat from the isothermal heat-sink to the radiator and vice versa;
  D. a phosphoric acid moisture cell in thermal contact with the isothermal heat sink;
  E. means for passing the moist gas through the cell; and
  F. means for measuring an electrical current in the cell and thereby determining the amount of moisture in the moist gas; and
  G. means for passing electrical current through the Peltier heater-cooler in a cell-heat-removing direction thereby removing heat from the heat sink and thereby from the cell when the cell has a temperature above the measuring temperature; and
  H. means for passing electrical current through the Peltier heater-cooler in a cell-heat-adding direction, opposite to the cell-heat-removing direction, thereby adding heat to the heat sink and thereby to the cell when the cell has a temperature below the measuring temperature; and
  I. means for maintaining the temperature of the cell at the given measuring temperature.

2. The apparatus of claim 1 wherein the isothermal heat-sink is made from metal.

3. The apparatus of claim 1 wherein the radiator is made of metal.

4. The apparatus of claim 1 which further comprises:
  J. a source of moist gas at superatmospheric pressure;
  K. a conduit in fluid communication with the moist gas source and the inlet of the cell;
  L. a purge line in fluid communication with the conduit having its junction with the conduit upstream of the cell;
  M. a valve in the purge line immediately adjacent to the junction;
  N. an isolation valve in the conduit downstream of the junction and immediately adjacent to the junction; and
  O. an outlet isolation valve in a conduit downstream of the cell.

5. An apparatus for accurately measuring, at a given measuring temperature within the range of about 0° to about 20° C., the water content of a moist gas containing less than 50 parts per million of water comprising:
  A. an isothermal heat sink (14);
  B. a radiator (20);
  C. a Peltier heater-cooler (24) thermally arranged between the isothermal heat sink (14) and the radiator (20), wherein said heater-cooler transfers heat from the isothermal heat sink (14) to the radiator (20) and vice versa;
  D. a phosphoric acid moisture cell (32) in thermal contact with the isothermal heat-sink (14);
  E. means (33, 34, 36) for passing the moist gas through cell (32);
  F. means (46) for measuring an electrical current in the cell (32); and thereby determining the amount of moisture in the moist gas; and
  G. means for passing electrical current through the Peltier heater-cooler in a cell-heat-removing direction thereby removing heat from the heat sink and thereby from the cell when the cell has a temperature above the measuring temperature; and
  H. means for passing electrical current through the Peltier heater-cooler in a cell-heat-adding direction, opposite to the cell-heat-removing direction, thereby adding heat to the heat sink and thereby to the cell when the cell has a temperature below the measuring temperature; and
  I. means for maintaining the temperature of the cell at the given measuring temperature; and
  J. a source (12) of moist gas at superatmospheric pressure;
  K. a conduit (36) in fluid communication with the moist gas source (12) and the inlet of the cell (32);
  L. a purge line (38) in fluid communication with the conduit (36) having its junction (39) with the conduit upstream of the cell (32);
  M. a valve (42) in the purge line (38) immediately adjacent to the junction (39);
  N. an isolation valve (44) in the conduit (36) downstream of the junction (39) and immediately adjacent to the junction (39); and
  O. an outlet isolation valve (53) in a conduit (36) downstream of the cell (32) wherein:
    said isothermal heat sink (14) is made from metal, has a cylindrical recess therein and has a planar heat conducting surface (18);
    said radiator (20) is made of metal, has a planar heat conducting surface (22) parallel to and juxtaposed a distance from the planar heat conducting surface (18) of the isothermal heat-sink (14);
    said Peltier heater-cooler (24) has a first and second juxtaposed parallel heat transfer surfaces (26, 27) thermally arranged between said isothermal heat-sink (14) and said radiator (20), with the first heat transfer surface (26) being in contact with the isothermal heat sink (14) and the second heat transfer surface being in contact with the radiator (20); wherein the electrical current can be passed through the Peltier heater-cooler (24) in either of two directions in order to heat one surface (26) of the heater-cooler and to cool the other surface (27) of the heater-cooler or vice versa; wherein means (29, 30) are provided for passing an electrical current in either direction through the heater cooler (24) in order to maintain the isothermal heat-sink (14) at a temperature between 0° C. and 15° C.;

said phosphoric acid moisture cell (32) is carried in said cylindrical recess (16) of the isothermal heat-sink (14), has a moist gas inlet (33) and a moist gas outlet (34) and is kept at substantially the same temperature as the isothermal heat sink.

* * * * *